(12) United States Patent
Suzuki

(10) Patent No.: US 6,475,177 B1
(45) Date of Patent: Nov. 5, 2002

(54) HEMOSTATIC AGENT INSERTING DEVICE

(75) Inventor: Shigeki Suzuki, Tokyo (JP)

(73) Assignee: New X-National Technology K.K., Tokyo (JP)

( * ) Notice: Subject to any disclaimer, the term of this patent is extended or adjusted under 35 U.S.C. 154(b) by 0 days.

(21) Appl. No.: 09/600,592

(22) PCT Filed: Oct. 12, 1999

(86) PCT No.: PCT/JP99/05604

§ 371 (c)(1),
(2), (4) Date: Jul. 19, 2000

(87) PCT Pub. No.: WO00/30553

PCT Pub. Date: Jun. 2, 2000

(30) Foreign Application Priority Data

Nov. 20, 1998 (JP) .......................... 10-330451

(51) Int. Cl.[7] .......................... A61F 13/20; A61B 17/08
(52) U.S. Cl. .......................... 604/11; 606/213
(58) Field of Search .......................... 604/11–18, 264, 604/59, 60; 606/213, 191

(56) References Cited

U.S. PATENT DOCUMENTS 4,890,612 A * 1/1990 Kensey
5,061,274 A * 10/1991 Kensey
5,192,302 A * 3/1993 Kensey et al.
5,391,183 A * 2/1995 Janzen et al.
5,437,631 A * 8/1995 Janzen
5,571,181 A * 11/1996 Li
5,716,375 A * 2/1998 Fowler
6,162,192 A * 12/2000 Cragg et al.

FOREIGN PATENT DOCUMENTS

| EP | 0 476 178 | 3/1992 |
| WO | WO 93/25255 | 12/1993 |
| WO | WO 95/05206 | 2/1995 |
| WO | WO 96/05772 | 2/1996 |
| WO | WO 96/24290 | 8/1996 |

* cited by examiner

Primary Examiner—Dennis Ruhl
(74) Attorney, Agent, or Firm—Crowell & Moring LLP

(57) ABSTRACT

A hemostatic material insertion device is provided for simplifying hemostasis of the puncture wound in a blood vessel. The device comprises a cartridge charged with hemostatic material, a hollow sheath which holds the cartridge, an ejecting piston portion which forms one unit with the sheath at the rear end of the sheath and is used for pushing out the hemostatic material charged in the cartridge, a guide knob to slide the cartridge inside the hollow sheath and a stopping device affixed to the front end of said hollow sheath. Further, methods of using a hemostatic material insertion device are provided.

11 Claims, 11 Drawing Sheets

HEMOSTATIC AGENT INSERTING DEVICE

BACKGROUND OF THE INVENTION

The present invention relates to a hemostatic material insertion device for sealing a puncture portion in a blood vessel to stop bleeding, as well as the method.

BACKGROUND ART

In special medical operations, such as a cardiac catheterization, a percutaneous diagnosed contract, a percutaneous transluminal coronary angioplasty (PTCA) or a percutaneous transluminal coronary reconstruction (PTCR), in general, a catheter or other device is percutaneously inserted into an artery from the inguinal region or the femoral region. After that, it is provided to the operation site, and thereby a minimally invasive operation is made.

In order to make the insertion of devices, such as catheters, easier during these operations, the arterial puncture portion must be expanded by a sheath, and followed by appropriate treatments for the completion of the operations. Additionally, after the operations, the sheath must be removed, and the puncture foramen must be closed.

Provided a puncture foramen is small, the hemostasis could be achieved simply by the application of digital pressure. However, in cases like blood vessel operations, the use of a catheter having a large diameter is much more advantageous, thus an operation is conducted using a sheath with a relatively large diameter.

However, digital pressure must be applied for a long time to achieve hemostasis of the puncture foramen after the operation using the sheath with a larger diameter. Consequently, because a patient must be immobilized until the sealing of the puncture foramen is completed, the procedure is painful and uncomfortable for the patient.

Additionally, it is not easy to seal the foramen perfectly by this procedure, and there is a tendency for the foramen to come open again after it is sealed. Therefore, the patients are required to remain in the hospital for 24 hours or longer.

Recently, a device, which stops bleeding by filling hemostatic materials, such as collagen, into the puncture foramen, was developed in order to seal the puncture foramen after the insertion of catheter, and the like, by using a sheath with a larger diameter, and the procedure of necessary operations. Thus, the device is being proposed to make it easier sealing a puncture foramen caused by cardial operations, and the like, which use a sheath with a larger diameter.

However, the hemostatic devices for puncture foramens, which have been available so far, use methods that involve pushing and filling a hemostatic material, such as collagen, into the puncture foramen. As a result, an excess of hemostatic material can easily get into an arterial canal located below the puncture foramen. In order to avoid the filling of excess hemostatic material, complicated devices are used, which require fairly high skill. Therefore it has been desired to develop a hemostatic material insertion (injection) device that is more simple and convenient to be used.

SUMMARY OF THE INVENTION

Therefore the purpose of the present invention is to provide a hemostatic material insertion device for sealing a puncture foramen by simple methods to stop bleeding, which does not require complicated devices, and with which filling arterial canals unnecessarily with excess hemostatic materials does not occur. Furthermore, another purpose is to provide methods for sealing a puncture foramen using the inventive device.

The first fundamental feature of the present invention is a hemostatic material insertion device for a puncture foramen comprising;

(a) A cartridge charged with hemostatic material, which is injected into the puncture foramen, (b) A hollow sheath which holds the said cartridge, (c) An ejecting piston portion pushing out the hemostatic material charged in the cartridge, which is united with the said sheath at the rear end of the sheath, (d) A guide knob to slide the said cartridge inside the hollow sheath, and (e) A stopping device equipped on the front end of the said hollow sheath, and the said cartridge charged with the hemostatic material is inserted into the puncture foremen by adjusting to set to the depth of the puncture foremen by means of the stopping device equipped at the front end of the sheath, then the said cartridge inserted into the puncture foramen is drawn back out of the puncture foramen by backward slide using the guide knob in the sheath, thus filling the puncture foramen with a hemostatic agent from the cartridge by means of the ejecting piston in the cartridge, united with the sheath.

Therefore, the above mentioned hemostatic material injection device of the present invention uses a cartridge which has already been charged with the hemostatic material, so that its insertion into the puncture foramen can be adjusted to the actual depth of the puncture. Thus one characteristic of this device is that unnecessary excess hemostatic material is not inserted into the inside of an arterial canal located under the puncture foramen.

For that purpose, in another embodiment of the device, the front tip of the cartridge has a tapered structure. As a result, the structure makes the insertion into the puncture foramen easier.

In addition, in a variation of the first embodiment, the tapered structure at the tip of the cartridge has been cut, and the filling of the hemostatic material, which is charged in the cartridge, into the puncture foramen is performed easily.

Based on the embodiments mentioned above, the device of a further embodiment of the present invention provides a hollow guide sheath inserted into a puncture foramen. This facilitates insertion of the cartridge charged with hemostatic material, and provides that both the hollow guide sheath and the cartridge are moved synchronously.

In short, through the hollow guide sheath inserted into a puncture foramen beforehand, the cartridge charged with the hemostatic material is inserted into the puncture foramen. After that, both the hollow guide sheath and the cartridge are drawn back out of the puncture foremen by sliding them using the guide knob in the sheath. The puncture foramen is simultaneously filled with the hemostatic agent charged in the cartridge by an ejecting piston in the cartridge.

A characteristic procedure of the hemostatic material insertion device of the present invention is one in which hemostatic material is filled into a puncture foramen. The procedure results from the fact that th e hemostatic agent charged in the cartridge is not inserted (filled) by pushing it out per se. Instead, it remains inside the puncture foramen while the cartridge, which was charged with the hemostatic material and which was originally inserted into the puncture foramen, is drawn out of the puncture foramen. Therefore, by this special characteristic, excess hemostatic material is not filled into a blood vessel under the puncture wound, and hemostasis of the puncture foramen can be accomplished with a high degree of safety.

A further embodiment of the present invention provides a method for sealing the puncture foramen to stop bleeding by using the aforementioned hemostatic material insertion device. More definitely, it provides a method to stop bleeding of the puncture foramen by inserting hemostatic material into the puncture foramen, which method has the following characteristics:

First, the cartridge charged with the hemostatic material is inserted into the puncture foramen. Next, by sliding the cartridge back within a sheath using a guide knob, the cartridge is drawn out of the puncture foramen. At the same time, the hemostatic material, charged in the cartridge within the puncture foramen is filled into the puncture foramen by means of an ejecting piston contacting the cartridge that is united with the sheath.

In a further embodiment the present invention provides a method for sealing the puncture foramen to stop the bleeding by using the aforementioned second hemostatic material insertion device. More concretely, it provides a method to stop bleeding of the puncture foramen by the hemostatic material inserted into the puncture foramen, which has the following characteristics:

First, the cartridge, charged with the hemostatic material, is inserted into the puncture foramen using a hollow sheath. Second, both the cartridge and the guide sheath are drawn out of the puncture foramen by sliding them back within the sheath using the guide knob. Simultaneously, the hemostatic material, charged in the cartridge within the puncture foramen, is filled into the puncture foramen wound by means of an ejecting piston contacting the cartridge that is united with the sheath.

BRIEF DESCRIPTION OF THE DRAWINGS

FIG. 6 shows the structure of a hollow guide sheath of the second embodiment.

FIG. 7 shows the structure of a cartridge charged with the hemostatic material of the second embodiment.

FIG. 9 shows the structure for the hollow sheath of the second embodiment.

DESCRIPTION OF THE REFERENCE NUMERALS

Figure 1:
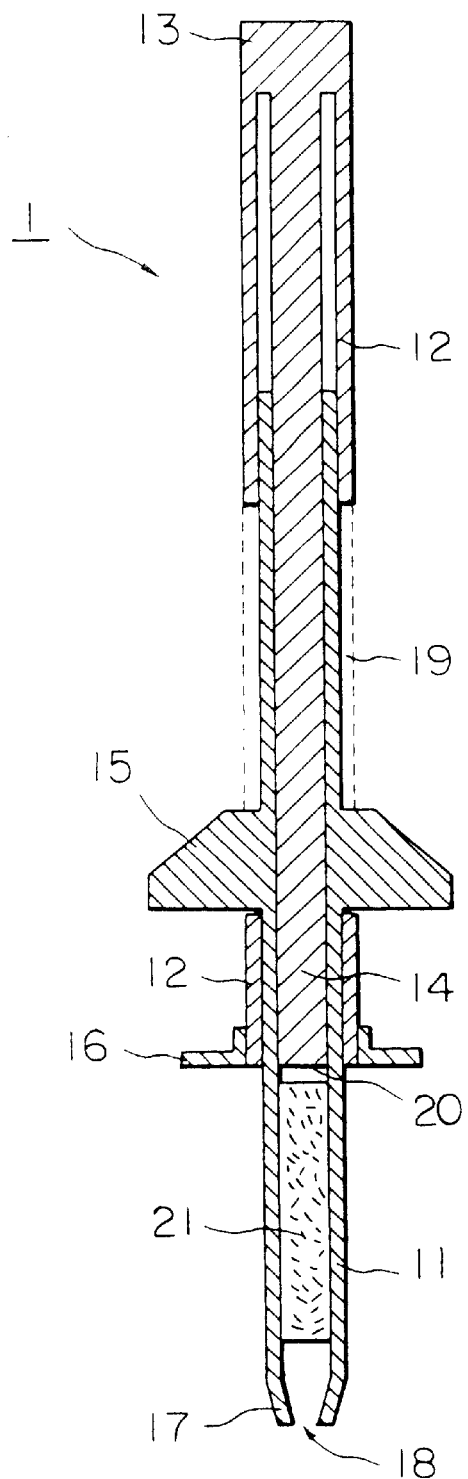
FIG. 1 is a vertical section showing the structure of the first embodiment of the hemostatic material insertion device of the present invention.

1 Hemostatic material injection device
8 Cartridge opened tip
11 Cartridge
12 Hollow sheath
13 Rear end of hollow sheath
14 Ejecting piston part
15 Guide knob
16 Stopping device
17 Cartridge tip portion
18 Opened part of tip
19 Opened groove
20 Ejecting piston part tip portion/front end
21 Hemostatic material
31 Puncture foramen
32 Blood vessel
40 Hemostatic material injection device
41 Hollow guide sheath
42 Cartridge
43 Hollow sheath
45 Ejecting piston part
46 Guide knob
47 Guide knob
48 Stopping device
50 Cartridge front tip
51 Groove
53 Opened groove

DESCRIPTION OF THE PREFERRED EMBODIMENTS

The hemostatic material insertion device of the present invention uses a cartridge which has already been charged with hemostatic material, the cartridge is inserted directly into a puncture foramen or through a hollow guide sheath. After that, the device fills the puncture foramen with hemostatic material by means of gradually withdrawing the cartridge charged with the hemostatic material from the puncture foramen. In this case, pulling the cartridge from the puncture foramen is accomplished by the hollow sheath, which holds the cartridge.

On the other hand, the insertion of the cartridge, charged with the hemostatic material into the puncture foramen, is adjusted to set it to the depth of the puncture foramen. Consequently, the tip of the cartridge will not be inadvertently inserted into the blood vessel at the lower part of the puncture wound. Such adjustment to set the cartridge insertion to the depth of the puncture foramen is made by the stopping device installed at the front tip of the sheath.

The following procedure is needed in order to fill the inside of the puncture foramen with the hemostatic material charged in the cartridge by removing the cartridge charged with the hemostatic material, from the puncture foramen. The cartridge is slid back inside the sheath, and the hemostatic material remains in the puncture foramen because of contact between the ejecting piston and the cartridge, which is united with the sheath.

As a result of the above-mentioned special construction, the hemostatic material insertion device of the present invention has advantages not only because it is simple and convenient, but also because it prevents inadvertent filling of the hemostatic material into the blood vessel under the puncture wound. Therefore, the use of the hemostatic material insertion device of the present invention provides special characteristics not provided when using conventional hemostatic material insertion devices such as the ability to achieve hemostasis of the puncture foramen without requiring a high level of skill.

EXAMPLES

The following are more detailed explanations of the hemostatic material insertion device of the present invention referring to the figures.

FIG. 1 shows a vertical section of the hemostatic material insertion device according to the first embodiment, which possesses the basic structure for the hemostatic material insertion device of this invention.

In the figure, the hemostatic material insertion device 1 consists of the following parts. The cartridge 11 charged with the hemostatic material 21 which is to be inserted into the puncture foramen, the hollow sheath 12 which holds the aforementioned cartridge, the ejecting piston part 14 which is united with the sheath 12 at the rear end 13 of the sheath 12, and which pushes the hemostatic material 21 out, the guide knob 15 which causes the cartridge 11 to slide inside the hollow sheath 12, and the stopping device 16 equipped at the front tip of the hollow sheath 12.

The tip portion 17 of the cartridge 11, charged with the hemostatic material 21, has a slightly tapered shape in order to make insertion into the puncture foramen easier. The diameter of the opened tip portion 18 at the tip portion 17 is made slightly narrower than the inside diameter of the cartridge 11. As a result, the charged hemostatic material can be expanded during its release from inside the cartridge 11, and can fill the inside of the puncture foramen compactly when the charged hemostatic material is pushed out by the tip portion 20 of the ejecting piston part 14.

It is acceptable to incise the tip portion 17 of the cartridge 11 in order to make it easier for the hemostatic material 21 charged in the cartridge to leave the cartridge and fill the inside of puncture foramen wound.

There is a stopping device 16 installed at the front tip of the hollow sheath 12 holding the cartridge 11 in order to prevent the insertion of the cartridge any further than the depth of the puncture foramen. For example, such stopping device 16 can be one which slides freely on the outside of the hollow sheath 12, and which adjusts and sets the length of the inserted portion of the cartridge 11, for example, that is like a screw for fixing.

In the hemostatic material insertion device 1 of the present invention, the hemostatic material 21 in the cartridge 11 remains and fills the puncture foramen when forced out of the opened tip 8 of the cartridge 11. This results from the movement of the front end 20 of the ejecting piston part 14 which is united with the hollow sheath by means of sliding the cartridge into the hollow sheath 12. In order to slide the cartridge 11 inside the hollow sheath 12, the guide knob 15 is installed on the cartridge 11. In addition, for example, the opened groove 19 is constructed for free movement of the guide knob 15 on both sides of the hollow sheath 12, where the guide knob is inside the opened groove 19. Consequently, the guide knob 15 can be utilized. Therefore, the possible distance for the backward slide of the guide knob 15 within the opened groove 19 is sufficient as long as the length for the insertion of the cartridge 11 into the puncture foramen is appropriately set.

In the hemostatic material insertion device of the present invention, the cartridge 11 is slid backwards inside the hollow sheath 12 which holds the cartridge 11 charged with the hemostatic material 21. Regarding the distance that makes the backward slide possible for this case, it is also sufficient as long as the insertion length of the cartridge 11 is at least as long as the puncture foramen.

The hemostatic material 21 in the cartridge 11 is charged close to the front end 20 of the ejecting piston part 14 equipped inside the cartridge 11. Therefore, following the cartridge's backward slide inside the hollow sheath 12, the ejecting piston part 14 is united and fixed to the said hollow sheath. Consequently, the hemostatic material 21 is pushed out of the cartridge, and remains in and fills the inside of the puncture foramen.

The following explains the method of insertion of the hemostatic material into the puncture foramen by using the hemostatic material insertion device according to the first example of this invention.

In cardiac catheter surgeries using large diameter sheaths, such as percutaneous transluminal coronary angioplasty (PTCA) or percutaneous transluminal coronary reconstruction (PTCR), the length of the insertion part of the cartridge 11 charged with the hemostatic material is adjusted by moving the stopping device equipped at the front end of the hollow sheath. By the procedure, when the surgeries are finished, the length of the insertion part of the cartridge becomes the same as the depth of the puncture foramen after the sheath is removed.

Figure 2:
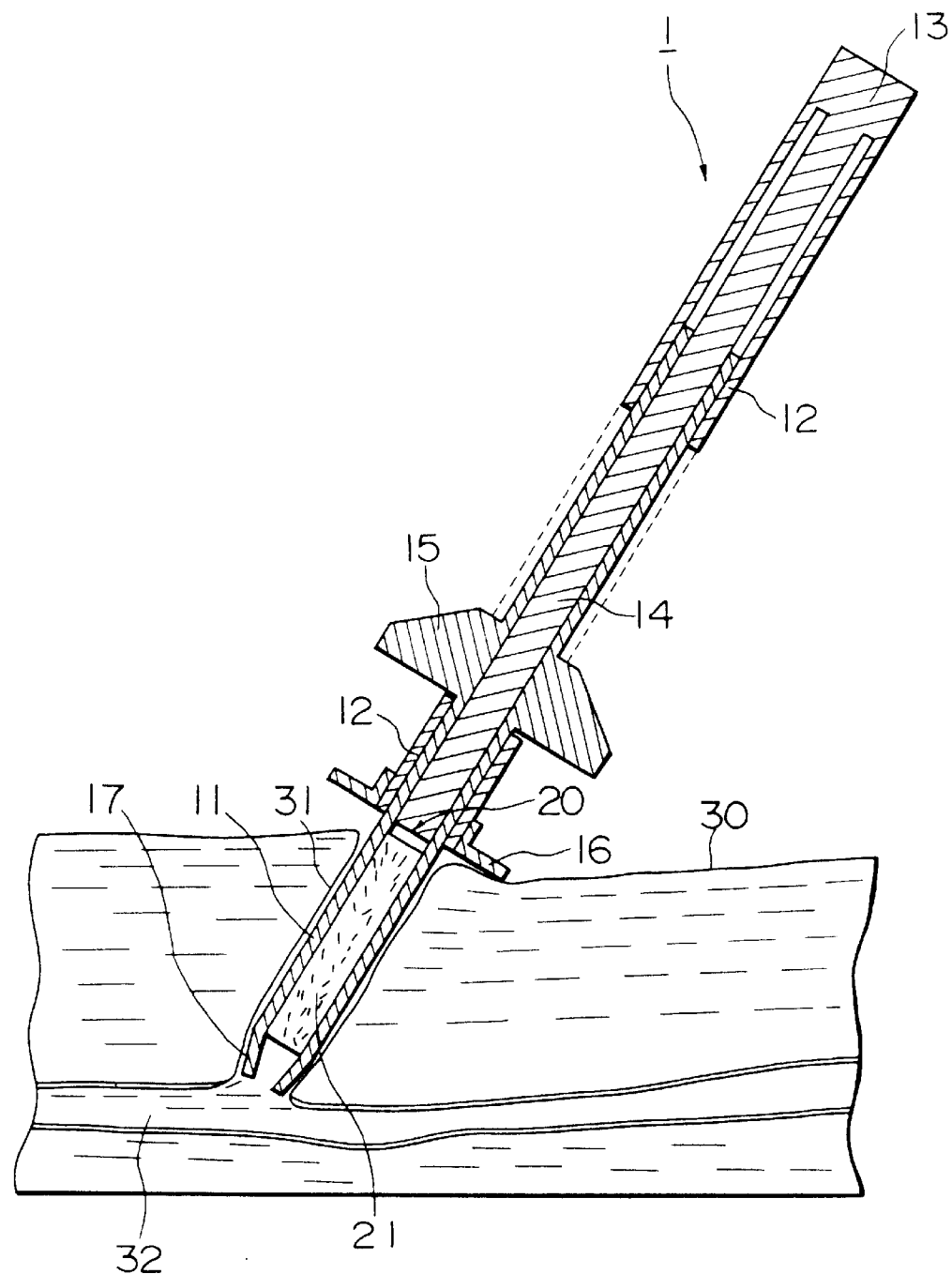
FIGS. 2, 3, and 4 are vertical sections schematically showing how to insert the hemostatic material into a puncture foramen according to the first embodiment of the present invention.

As shown in FIG. 2, the device is then inserted inside the puncture foramen 31 located on the skin surface 30. To insert the cartridge 11 inside the puncture foramen, the hemostatic material injection device 1 is fixed on the skin surface 30 by means of the stopping device 16, which is adjusted to the depth of the puncture foramen. Consequently, the tip portion 17 of the cartridge 11 is never inserted into the blood vessel 32 located below the puncture wound.

Figure 3:
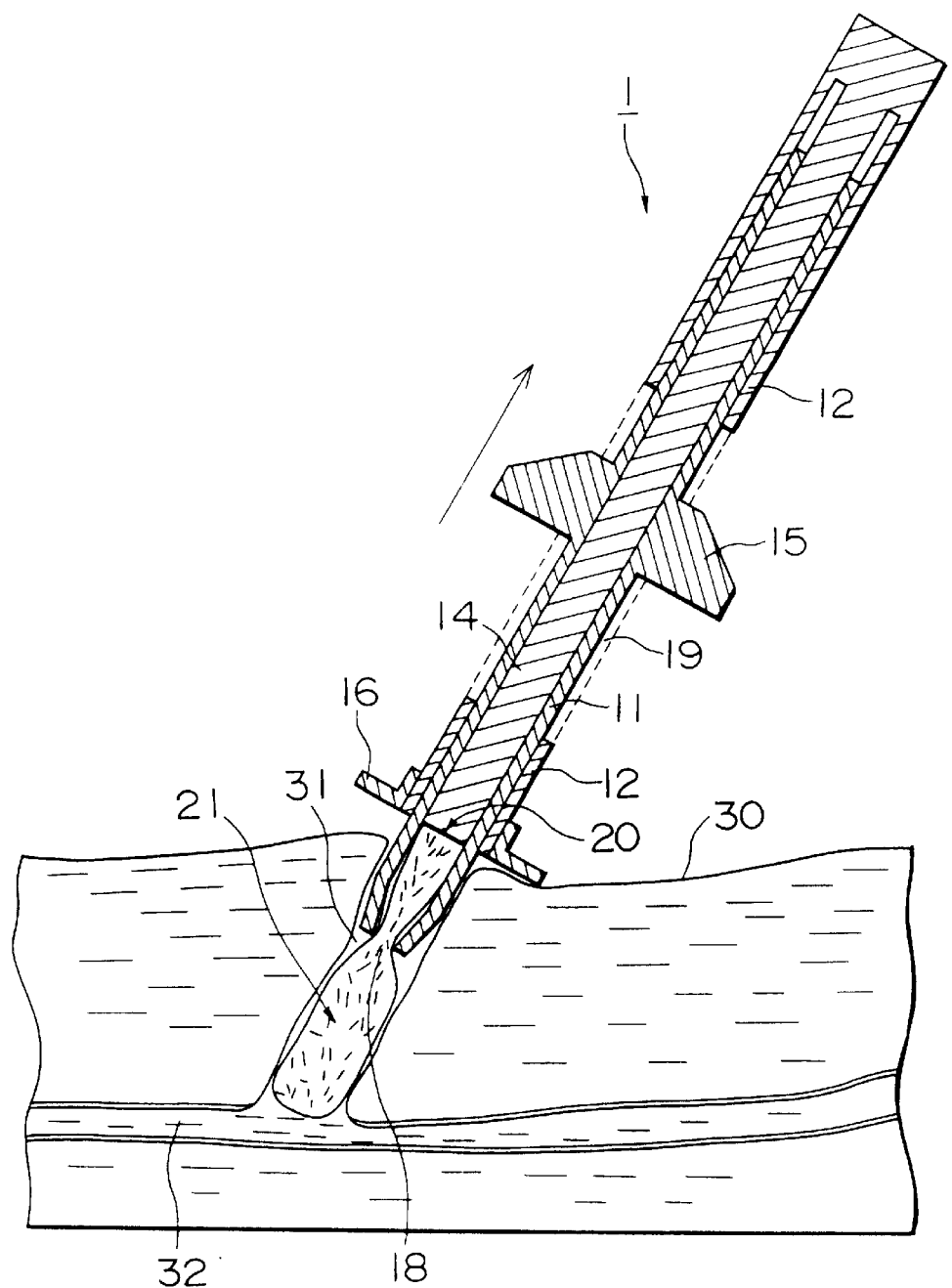

As shown in FIG. 3, this condition is maintained, with the stopping device fixed on the skin surface 30, the cartridge 11 inserted in the puncture foramen 31 is slid backwards (shown by an arrow in FIG. 3) by the guide knob 15 in the hollow sheath 12.

By the backward slide of the cartridge 11, the cartridge is drawn out from the puncture foramen 31. Simultaneously, the hemostatic material 21 in the cartridge 11 is pushed out of the opened tip 18 of the cartridge 11 by the movement of the front end 20 of the ejecting piston part 14. Additionally, since the inner diameter of the opened tip 18 is slightly narrower than that of the cartridge 11, the hemostatic material begins to expand inside the puncture foramen as released, and remains and fills the puncture foramen compactly.

Figure 4:
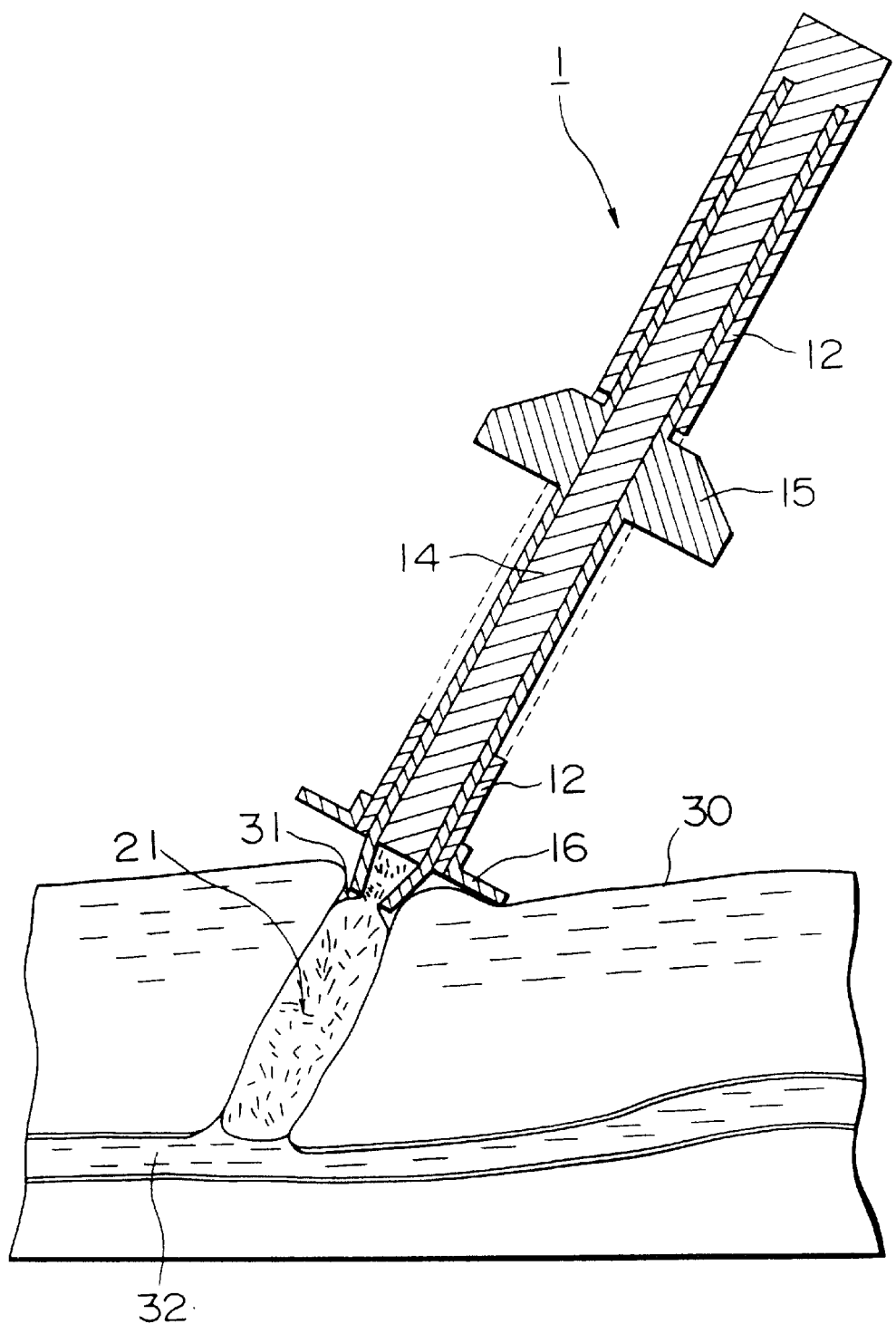

When the cartridge 11 is completely pulled out from the puncture foramen, as shown in FIG. 4, the hemostatic material 21 is inserted compactly into the puncture foramen 31. Simultaneously, the device 1 is removed, and the insertion of the hemostatic material 21 into the puncture foramen is completed.

Figure 5:
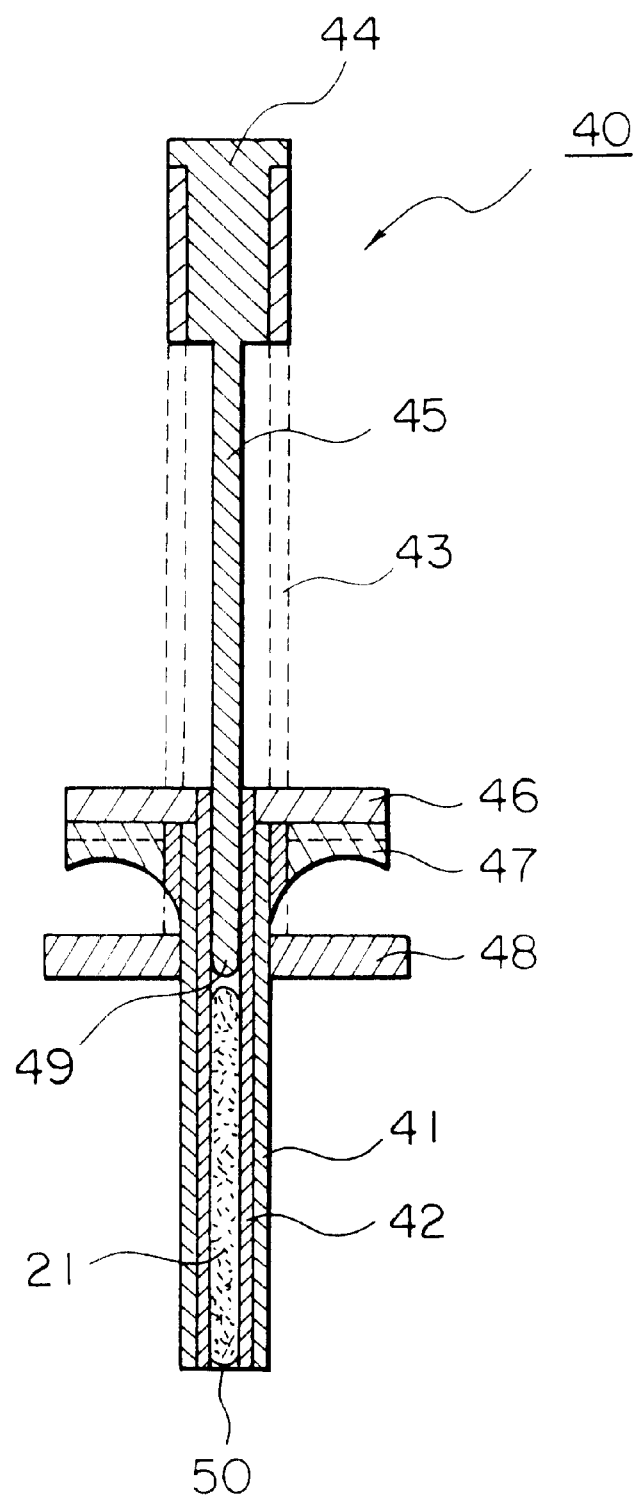
FIG. 5 is a vertical section showing the structure for the second embodiment of a hemostatic material insertion device of the present invention.

FIG. 5 shows a vertical section of the second example of the hemostatic material insertion device.

In the figure, the hemostatic material insertion device 40 comprises a hollow guide sheath 41 inserted into the puncture foramen, a cartridge 42 charged with the hemostatic material 21, which is inserted into the hollow guide sheath 41, a hollow sheath 43 maintaining the aforementioned cartridge, a ejecting piston 45 pushing out the hemostatic material 21 in the cartridge 42 which is united with the hollow sheath 43 at the rear end 44 of the sheath 43, guide knobs 46 and 47 which cause both the cartridge 42 and the guide sheath 41 to slide inside of the hollow sheath 43, and a stopping fixture 48 equipped at the front tip of the hollow sheath 43.

In the second example, the insertion of the hemostatic material, which is charged in the cartridge 42, into the puncture foramen is performed in the same way as the first example. In short, the hemostatic material 21 in the cartridge 42 remains in and fills the puncture foramen. This is caused by the front end 49 of the ejecting piston 45, which is united with the hollow sheath by means of sliding the cartridge 42 backwards inside the hollow sheath 43.

In the second example, some components differ from the first embodiment of the device. In order to simplify the insertion of the cartridge 43 charged with the hemostatic material into the puncture foramen, the cartridge 43 is inserted through the hollow guide sheath 41. Then the hollow guide sheath 41 and the cartridge are united, and slid backwards inside the sheath 43 using the guide knobs 46 and 47.

Figures 6A, 6B:
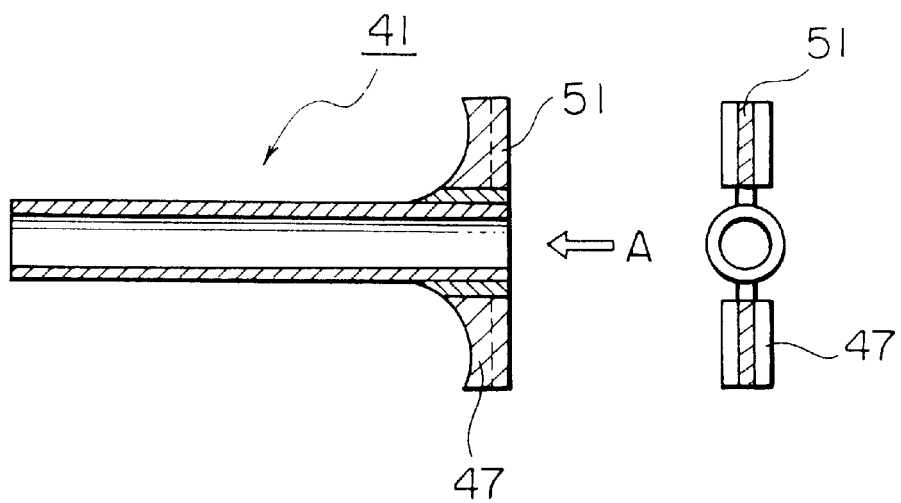
FIG. 6A is a vertical section of the said structure.
FIG. 6B is a front view seen from arrow A.
Figures 7A, 7B:
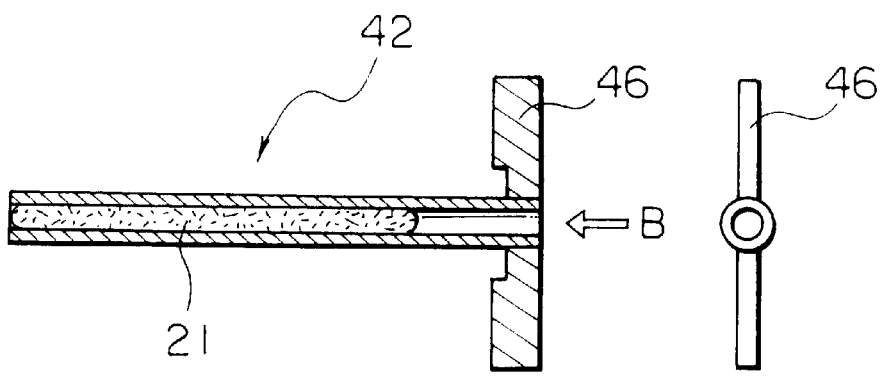
FIG. 7A is a vertical section.
FIG. 7B is a front view seen from arrow B.

FIG. 6 shows the vertical section of the hollow guide sheath 41, and FIG. 7 shows the vertical section of the cartridge 42 charged with the hemostatic material, which is inserted into the guide sheath 41.

The hollow guide sheath 41 used in the second example has an appropriate length and diameter in order to insert the device into the puncture foramen, and a pipe-shape in which the cartridge 42 can be inserted. Furthermore, the guide knob 47 is equipped at the end of the guide sheath, and in the guide knob 47, the groove 51 is equipped, in which the guide knob can be inserted in order to unite with the cartridge inside the guide sheath. FIG. 6 (b) shows the shape of the guide sheath of FIG. 6 (a) from the view of arrow A.

On the other hand, the cartridge 42 charged with the hemostatic material, which is put into the hollow guide sheath, has a diameter allowing insertion into the guide sheath 41. In addition, the guide knob 46, which is able to go into the groove 51 equipped in the knob 47 of the guide sheath 41, is provided at the end of the cartridge. FIG. 7 (b) shows the shape of the cartridge 42 shown in FIG. 6 (a) from the view of the guide knob 46 by arrow B.

The length of the guide sheath 41 coincides with that of the cartridge 42 at the ends, and the lengths, enough to be inserted, are appropriate.

Figure 8A:
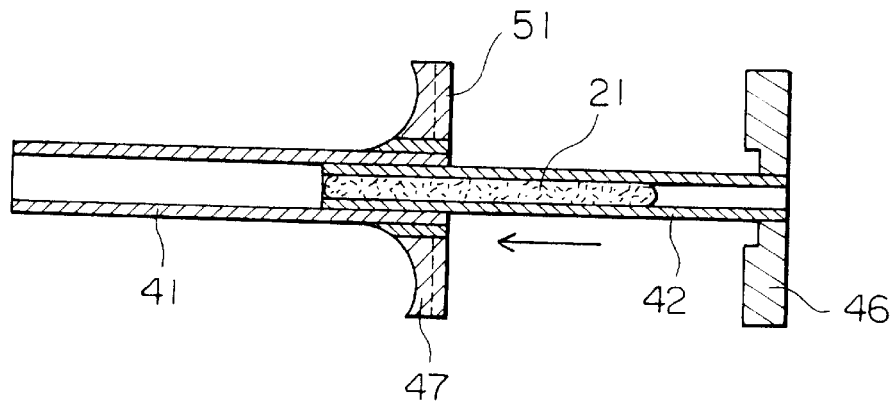
FIG. 8A is an illustration of how to insert a cartridge, charged with the hemostatic material of the second embodiment into a hollow guide sheath.
Figure 8B:
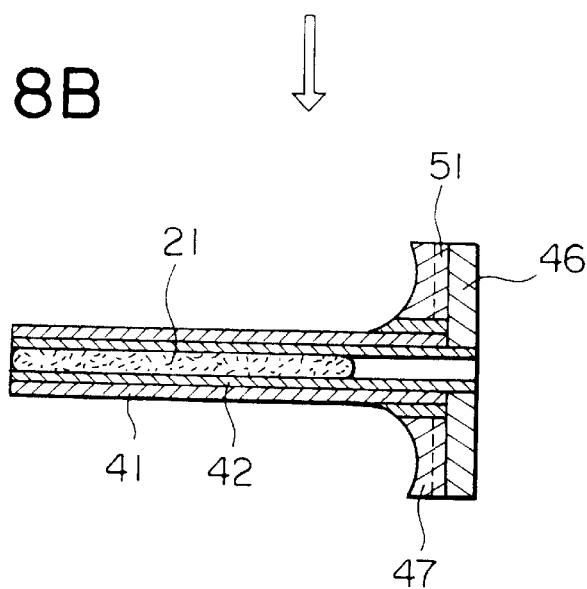
FIG. 8B illustrates a hollow guide sheath joined with a cartridge charged with the hemostatic material of the second embodiment.

FIG. 8 (a) and (b) depict a scenario where the cartridge 42, charged with the hemostatic material, is united with the hollow guide sheath 41. In other words, the cartridge 42 is put inside the hollow sheath inserted and into the puncture foramen (directed by the arrow in FIG. 8 (a)). Furthermore, the knob 46 of the cartridge 42 is put into the groove 51 equipped on the guide knob 47 of the sheath 41. As a result, the both of them are united.

Figure 9A:
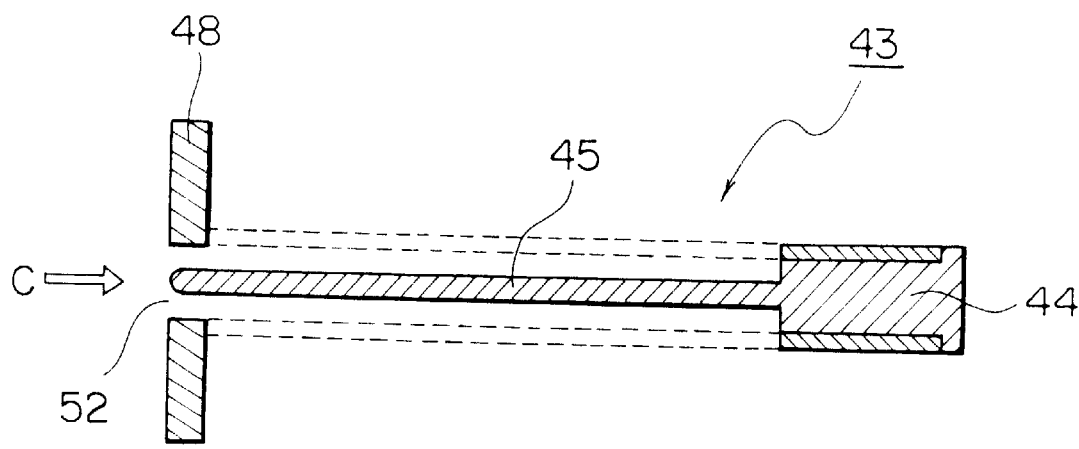
FIG. 9A is a vertical section.
Figure 9B:
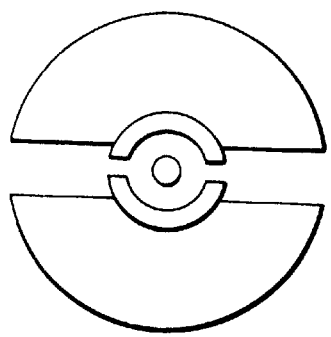
FIG. 9B is a front view seen from arrow C.
Figure 9C:
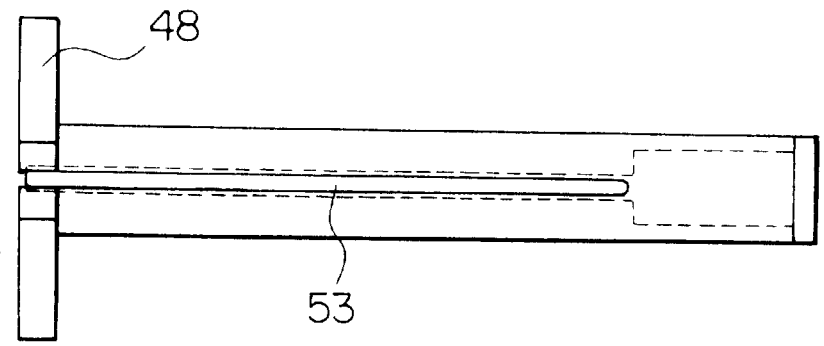
FIG. 9C is a front view seen from an opened groove.

So united, both the sheath 41 and the cartridge 42 charged with the hemostatic material 21 are slid backwards in the hollow sheath 43. As a result, the hemostatic material 21 in the cartridge 42 is injected into the puncture foramen by means of the ejecting piston. FIG. 9 shows the vertical section of the cartridge 43.

From the figure, the front end of the hollow sheath 43 has the stopping device 48 against the skin surface, and also has the opening part 52 to put the cartridge 42 (and the guide sheath 41 in one unit) into the hollow sheath 43. At its rear end 44, the ejecting piston 45 is united with the hollow sheath 43, which pushes the hemostatic material 21 out of the cartridge 42. Furthermore, the sheath 43 has the opening groove 53 at both sides, which is necessary for sliding the cartridge 42 (and the guide sheath 41 in one unit) backwards inside of the sheath 43. In addition, the movement of the cartridge is performed by the structure sliding the guide knobs 46 and 47 through the opening groove 53. Therefore, the possible distance for the backward slide of these guide knobs in the opening groove 53 is sufficiently long and proportionate to the insertion length of the cartridge 42 (and the guide sheath 41) into the puncture foremen. Moreover, FIG. 9 (b) shows the opening groove 52 of the hollow sheath 43 from the view of the arrow C in FIG. 9 (c), and FIG. 9 (b) shows the front view of the opening groove 53 of the hollow sheath 43.

The following is an explanation of the method of insertion of a hemostatic material into the puncture foramen by using the hemostatic material insertion device according to the second example of the invention, as described above.

Figure 10:
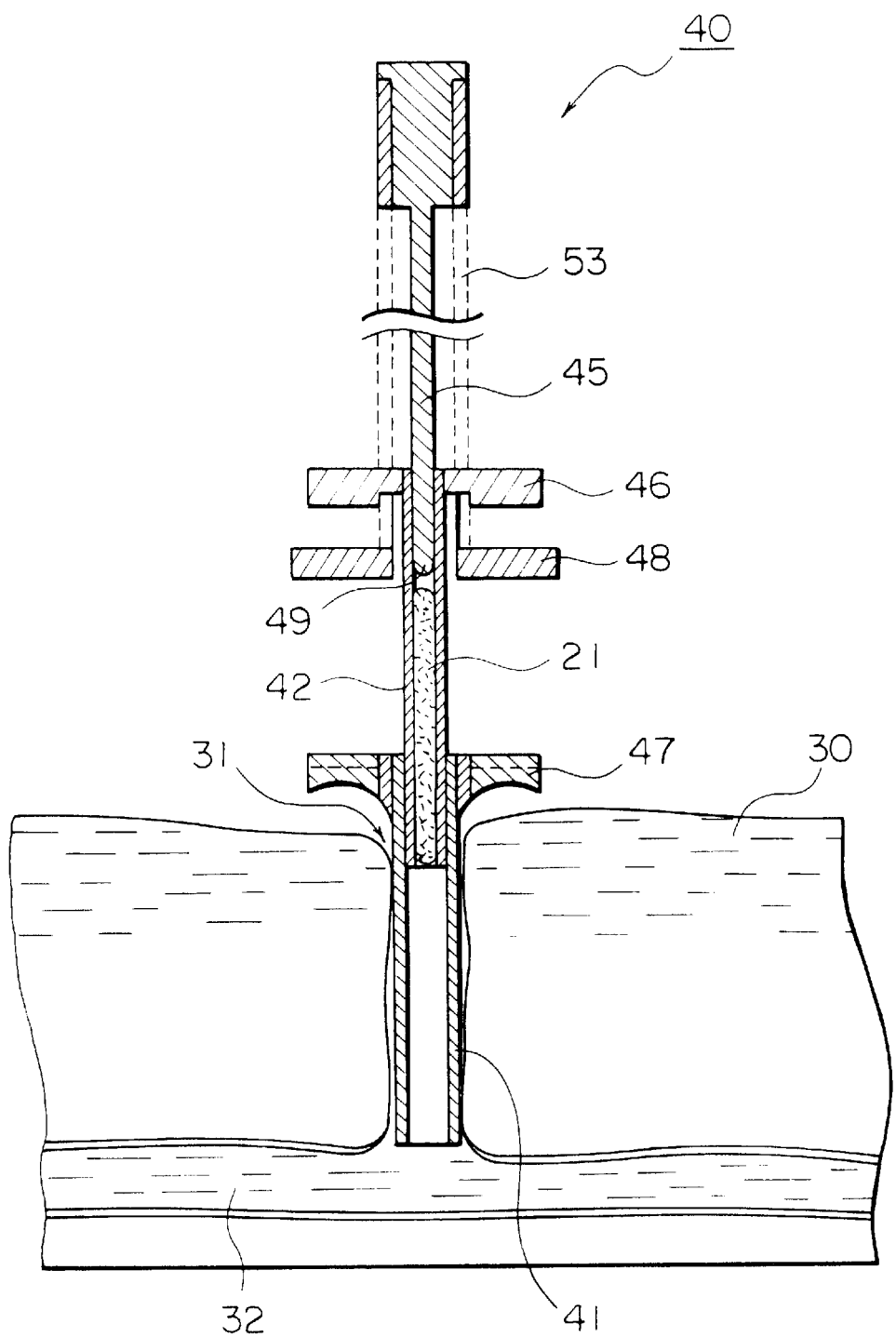
FIGS. 10, 11 and 12 are vertical sections outlining how to fill a puncture foramen with the hemostatic material of the present invention.

First, as shown in FIG. 10, after a surgery using a large diameter sheath, such as percutaneous transluminal coronary angioplasty (PTCA) or percutaneous transluminal coronary reconstruction (PTCR), the hollow guide sheath 41 is inserted into the puncture foramen so that the insertion length corresponds to the depth of the puncture foramen. Then, the cartridge 42 charged with the hemostatic material is put into the guide sheath 41 from the front side of the cartridge 42. Simultaneously, both the guide sheath 41 and the cartridge 42 are united by means of getting the knob 46 into the knob 47.

Figure 11:
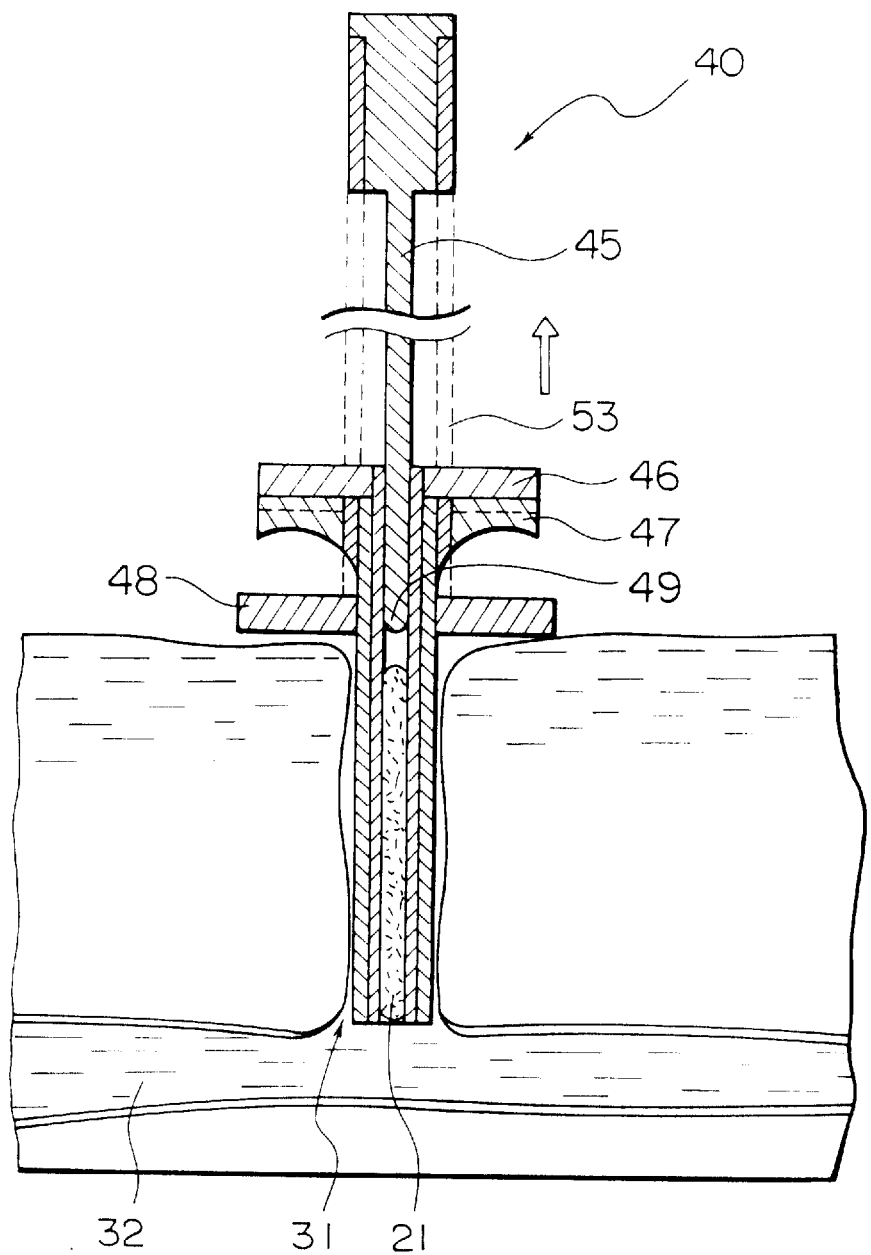

In this condition, as shown in FIG. 11, the insertion of the cartridge 42 into the puncture foramen is easily accomplished through the guide sheath 41. At the same time, this hemostatic material insertion device is fixed on the skin surface 30 by means of the stopping device 48 equipped at the front tip of the hollow sheath 43. As a result, the front tip 50 of the cartridge 42 is never inserted into the blood vessel 32 below the puncture wound.

This position is maintained with the stopping device fixed on the skin surface 30. In this condition, the cartridge 42 (and the guide sheath 41 in one unit) inserted in the puncture foramen 31 is slid backwards (direction indicated by the arrow in FIG. 11) by using the guide knob 46 (and the knob 47 in one unit) in the opening groove 53 inside the hollow sheath 43.

By sliding the cartridge 42 (and the guide sheath 41 in one unit) backwards, the cartridge 42 is drawn out of the puncture foramen 31 with the guide sheath 41 in one unit. Simultaneously, the hemostatic material 21 in the cartridge 42 gets pushed out from the front opening part 50 of the cartridge by the action of the front end 49 of the ejecting piston 45, and remains in the puncture foramen and accumulates compactly.

Figure 12:
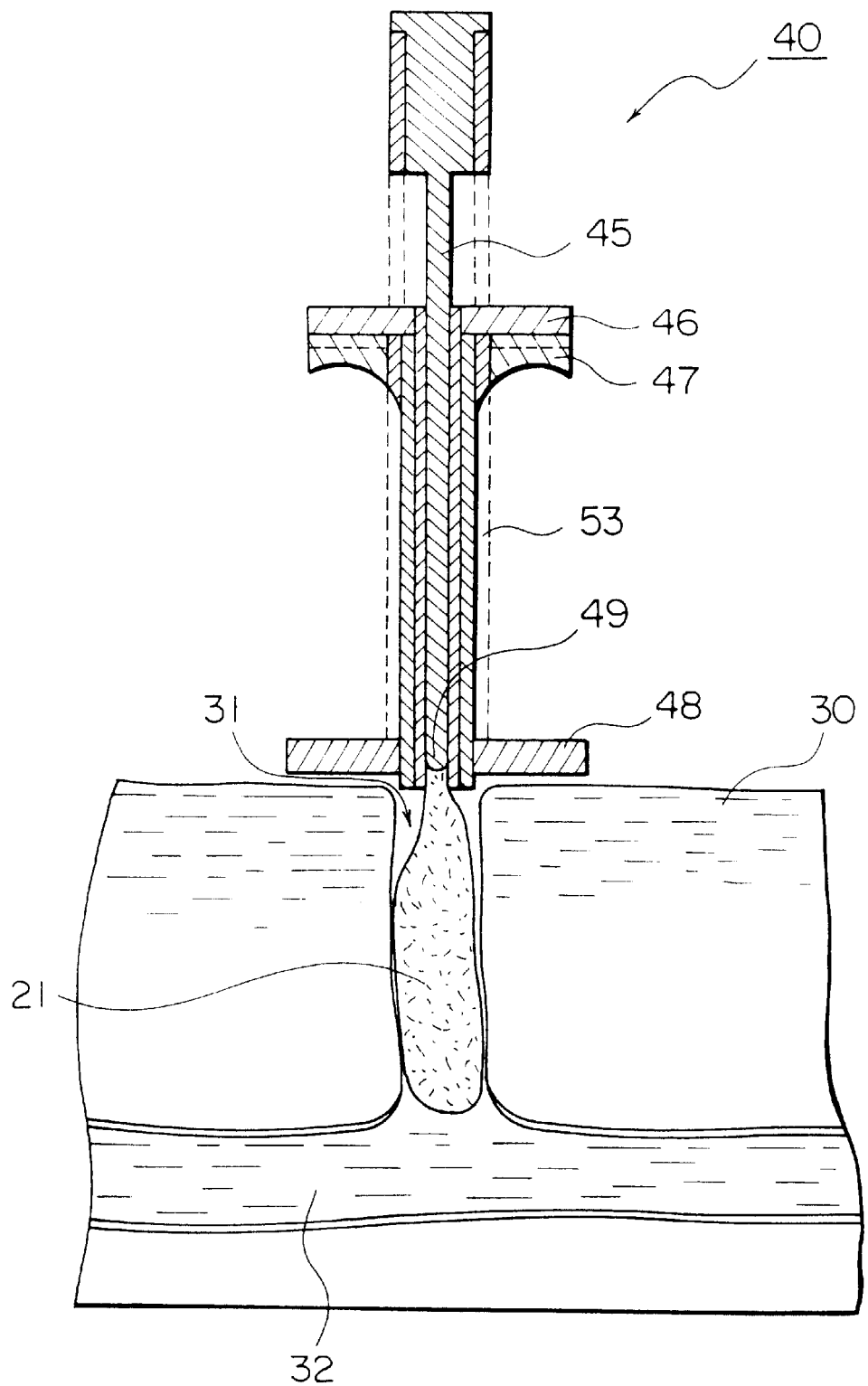

As shown in FIG. 12, when the cartridge 42 (and the guide sheath 41 in one unit) is completely pulled out from the puncture foramen, the hemostatic material 21 is inserted compactly into the puncture foramen 31. At the same time, the device is removed and the inserting of the hemostatic material 21 into the puncture foramen is completed.

In addition to the basic construction described above, the hemostatic material insertion device of the present invention optionally includes various modifications, all of these would all be included within the scope of this invention.

By the above-mentioned procedures, the hemostatic material can be easily inserted into the puncture foramen. Examples of hemostatic materials include collagen, which is conventionally used for various hemostatic purposes, or soluble hemostatic cellulose. Soluble hemostatic cellulose produces good results as a hemostatic material for this injection device.

It is possible to install a guide wire into the center of the hemostatic agent insertion device of the present invention in order to assure the insertion of the cartridge inside the puncture foramen. However, such a guide wire is not always necessary. Particularly, considering that hemostatic procedures for the puncture foramen are done immediately following the removal of the sheath after a surgery, the insertion of the cartridge into the puncture foramen would be possible without it.

Of course, the hemostatic material insertion device of the present invention could be applied not only for hemostasis of the puncture foramen of blood vessels as described above, but also for hemostasis of body cavity surgeries.

As stated above, compared to hemostatic methods using the complicated conventional devices, the hemostatic agent insertion device of the present invention makes it easier to insert the hemostatic material into the puncture foramen. Furthermore, the risk of inadvertent injection of the hemostatic material into the blood vessel at the bottom of the puncture foramen is avoided due to the fact that the length of the cartridge inserted into the puncture foramen can be adjusted freely according to the depth of the puncture foramen.

In addition, the hemostatic material is inserted by pulling the cartridge charged with it not from the inside of the puncture foramen. For this reason, compared to the conventional insertion, it does not require technical skills, consequently, a broader medical application is possible.

What is claimed is:

1. A hemostatic material insertion device for a puncture foramen, comprising:
   a cartridge charged with hemostatic material;
   a hollow sheath which holds said cartridge at one end of said sheath;
   an ejecting piston portion connected to said sheath at the other end of said sheath;
   a guide knob located on a side of said hollow sheath; and
   a stopping device equipped on said one end of said hollow sheath, wherein
   said stopping device is adapted to be positioned along said one end of said hollow sheath to enable the length of the cartridge extending beyond said stopping device to correspond to the depth of the puncture foramen,
   whereby when said cartridge is inserted into the puncture foramen and said cartridge is drawn back out of the puncture foramen by sliding said guide knob away from the puncture foramen, and said cartridge contacts said ejecting piston portion, the puncture foramen is filled with a hemostatic material.

2. A hemostatic material insertion device according to claim 1, wherein said cartridge has a tip portion and said tip portion is tapered.

3. A hemostatic material insertion device according to claim 2, wherein said tapered tip portion comprises an opening.

4. A hemostatic material insertion device according to claim 1, further comprising a hollow guide sheath that is capable of being used for the insertion of said cartridge into the puncture foramen, and wherein said hollow sheath and said cartridge are united.

5. A hemostatic material insertion device according to claim 1, wherein the hemostatic material is collagen or soluble hemostatic cellulose.

6. A hemostatic material insertion device according to claim 2, further comprising a hollow guide sheath that is capable of being used for the insertion of said cartridge into the puncture foramen, and wherein said hollow sheath and said cartridge are united.

7. A hemostatic material insertion device according to claim 3, further comprising a hollow guide sheath that is capable of being used for the insertion of said cartridge into the puncture foramen, and wherein said hollow sheath and said cartridge are united.

8. A method for stopping bleeding of a puncture foramen, comprising:
   inserting a cartridge charged with a hemostatic agent into the puncture foramen; and
   sliding a guide knob located on said cartridge along a hollow sheath to remove said cartridge from the puncture foramen and to move said cartridge into said hollow sheath, wherein
   said sliding causes an ejection piston on said hollow sheath to force the hemostatic agent from said cartridge to thereby fill the puncture foramen with the hemostatic agent.

9. A method for stopping bleeding of a puncture foramen according to claim 8, wherein said hemostatic agent is collagen or soluble hemostatic cellulose.

10. A method for stopping bleeding of a puncture foramen according to claim 8, wherein said inserting is carried out through a guide sheath.

11. A method for stopping bleeding of a puncture foramen according to claim 10, wherein said hemostatic agent is collagen or soluble hemostatic cellulose.

* * * * *